(12) United States Patent
Liu

(10) Patent No.: US 11,576,635 B2
(45) Date of Patent: Feb. 14, 2023

(54) SOURCE IMAGE DISTANCE ADJUSTABLE X-RAY IMAGING APPARATUS

(71) Applicant: SHANGHAI UNITED IMAGING HEALTHCARE CO., LTD., Shanghai (CN)

(72) Inventor: Wenqiang Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/000,390

(22) Filed: Aug. 24, 2020

(65) Prior Publication Data

US 2020/0383650 A1   Dec. 10, 2020

Related U.S. Application Data

(63) Continuation of application No. 15/859,545, filed on Dec. 31, 2017, now Pat. No. 10,751,013.

(30) Foreign Application Priority Data

Sep. 29, 2017   (CN) .......................... 201710908553.0

(51) Int. Cl.
   *A61B 6/00*   (2006.01)
(52) U.S. Cl.
   CPC ............ *A61B 6/4452* (2013.01); *A61B 6/447* (2013.01); *A61B 6/4441* (2013.01)
(58) Field of Classification Search
   None
   See application file for complete search history.

(56) References Cited

U.S. PATENT DOCUMENTS

| 4,365,343 A | 12/1982 | Grady et al. |
| 4,964,151 A | 10/1990 | Trotel |

(Continued)

FOREIGN PATENT DOCUMENTS

| CN | 104173069 A | 12/2014 |
| CN | 204468110 U | 7/2015 |

(Continued)

OTHER PUBLICATIONS

First Office Action in Chinese Application No. 201710908553.0 dated Mar. 27, 2020, 14 pages.

(Continued)

*Primary Examiner* — Christine S. Kim
(74) *Attorney, Agent, or Firm* — Metis IP LLC

(57) ABSTRACT

A source image distance (SID) adjustable X-ray imaging apparatus is provided. The X-ray imaging apparatus may include an arm including a first end and a second end, a first X-ray component arranged at the first end of the arm, and a second X-ray component arranged at the second end of the arm. The first X-ray component and the second X-ray component may be opposite to each other. The first X-ray component may be configured to generate X-rays or receive X-rays. The first end may include a first weight balancing mechanism. When the first X-ray component moves with respect to the first weight balancing mechanism, the SID of the X-ray imaging apparatus may change but the first weight balancing mechanism may maintain a center of gravity of the first end unchanged.

18 Claims, 11 Drawing Sheets

(56) References Cited

U.S. PATENT DOCUMENTS

| | | | |
|---|---|---|---|
| 6,402,374 B1* | 6/2002 | Boomgaarden | A61B 6/588 378/207 |
| 6,789,941 B1* | 9/2004 | Grady | A61B 6/504 378/197 |
| 8,461,277 B2 | 6/2013 | Dougherty et al. | |
| 2005/0199059 A1 | 9/2005 | Danz et al. | |
| 2009/0232282 A1* | 9/2009 | Belson | A61B 6/4423 378/209 |
| 2009/0296886 A1 | 12/2009 | Maltz et al. | |
| 2013/0028390 A1* | 1/2013 | Kalenyak | H02K 7/09 378/197 |
| 2014/0003585 A1 | 1/2014 | Ling et al. | |
| 2015/0131775 A1 | 5/2015 | Yorkston et al. | |

FOREIGN PATENT DOCUMENTS

| | | |
|---|---|---|
| CN | 105852892 A | 8/2016 |
| WO | 2014129919 A1 | 8/2014 |

OTHER PUBLICATIONS

The Second Office Action in Chinese Application No. 201710908553.0 dated Sep. 9, 2020, 13 pages.

* cited by examiner

1100

```
┌──────────────────────────────────────────────────────┐
│ Moving a first X-ray component on a first end by a   │ ～ 1110
│ driving structure in a first direction with respect to a │
│ first weight balancing mechanism                     │
└──────────────────────────────────────────────────────┘
                            │
                            ▼
┌──────────────────────────────────────────────────────┐
│ Moving a weight by the driving structure in a second │ ～ 1120
│ direction opposite to the first direction            │
└──────────────────────────────────────────────────────┘
```

FIG. 11

SOURCE IMAGE DISTANCE ADJUSTABLE X-RAY IMAGING APPARATUS

CROSS-REFERENCE TO RELATED APPLICATIONS

This application is a continuation application of U.S. patent application Ser. No. 15/859,545, filed on Dec. 31, 2017, which claims priority to Chinese Patent Application No. 201710908553.0, filed on Sep. 29, 2017, the contents of which are hereby incorporated by reference.

TECHNICAL HELD

The present disclosure generally relates to a medical imaging apparatus, and more particularly, relates to a source image distance (SID) adjustable X-ray imaging apparatus and a method for adjusting the SID.

BACKGROUND

X-ray imaging technology is becoming increasingly popular. The corresponding X-ray or CT imaging apparatus generally includes an X-ray tube and an X-ray detector. The X-ray tube may generate X-rays to a scanning object (usually a patient). The X-ray detector may receive X-rays that pass through the object and generate a reading corresponding to the received X-rays. The X-ray tube and the X-ray detector may be arranged opposite to each other on two ends of a C-shaped arm or a G-shaped arm. The C-shaped arm or G-shaped arm may be able to rotate freely in all three dimensions and hence X-ray images from any angle or slice of the object may be obtained. However, the distance between the X-ray tube and the X-ray detector (which is referred to as source image distance (SID)) is conventionally fixed. Some X-ray imaging apparatuses may have certain complex mechanical and electrical structures to adjust the SID, but the arm is usually tilted or rotated after the adjustment because the center of gravity of the arm or the ends thereof change. The tilt or rotation of the arm may cause a change of scanning areas and create discontinuity or artifacts in X-ray images. Thus, it may be desirable to provide an X-ray imaging apparatus of which SID can be easily changed without causing any tilt or rotation of the arm.

SUMMARY

According to an aspect of the present disclosure, an X-ray imaging apparatus is provided. The X-ray imaging apparatus may include an arm including a first end and a second end, a first X-ray component arranged at the first end of the arm, and a second X-ray component arranged at the second end of the arm. The first X-ray component and the second X-ray component may be opposite to each other. The first X-ray component may be configured to generate X-rays or receive X-rays. The first end may include a first weight balancing mechanism. When the first X-ray component moves with respect to the first weight balancing mechanism, the first weight balancing mechanism may maintain a center of gravity of the first end unchanged.

In some embodiments, the first X-ray component may include an X-ray tube configured to generate X-rays. The second X-ray component may include an X-ray detector configured to receive at least part of the X-rays generated by the first X-ray component. The second end may include a second weight balancing mechanism. When the X-ray tube moves with respect to the first weight balancing mechanism, the first weight balancing mechanism may maintain a center of gravity of the first end unchanged. When the X-ray detector moves with respect to the second weight balancing mechanism, the second weight balancing mechanism maintains a center of gravity of the second end unchanged.

In some embodiments, the first weight balancing mechanism may include a driving structure and a weight. When the first X-ray component moves with respect to the first weight balancing mechanism, the driving structure may move the weight such that the first weight balancing mechanism maintains the center of gravity of the first end unchanged.

In some embodiments, a movement direction of the first X-ray component may be opposite to a movement direction of the weight.

In some embodiments, the driving structure may include a first transmission part, a second transmission part, and a gear engaged with the first transmission part and the second transmission part. The first transmission part may connect to the first X-ray component, and the second transmission part may connect to the weight.

In some embodiments, the driving structure may include a lead screw. A first part of the lead screw may connect to the first X-ray component, and a second part of the lead screw connects to the weight.

In some embodiments, a handedness of threads of the first part of the lead screw may be different from a handedness of threads of the second part of the lead screw.

In some embodiments, the arm may be a C-shaped arm or a G-shaped arm.

In some embodiments, the weight balancing mechanism may include a guiding rail and the first X-ray component may be configured to move on the guiding rail.

In some embodiments, the first X-ray component may move in a direction of toward or away the second end of the arm.

In some embodiments, a movement of the first X-ray component may cause a change of a Source Image Distance (SID) of the X-ray imaging apparatus.

According to another aspect of the present disclosure, an X-ray imaging apparatus is provided. The X-ray imaging apparatus may include an arm including a first end and a second end, a first X-ray component arranged at the first end of the arm, and a second X-ray component arranged at the second end of the arm. The first X-ray component and the second X-ray component may be opposite to each other. The first X-ray component may be configured to generate X-rays or receive X-rays. The first end may include a first weight balancing mechanism, and the first weight balancing mechanism may include a first driving structure and a first weight. When the first X-ray component moves with respect to the first weight balancing mechanism, the driving structure may move the weight in a direction opposite to a movement direction of the first X-ray component.

In some embodiments, the first X-ray component may include an X-ray tube configured to generate X-rays, and the second X-ray component may include an X-ray detector configured to receive at least part of the X-rays generated by the first X-ray component. The second end may include a second weight balancing mechanism and the second weight balancing mechanism may include a second driving structure and a second weight. When the X-ray tube moves with respect to the first weight balancing mechanism, the first driving structure may move the first weight in a direction opposite to a movement direction of the X-ray tube. When the X-ray detector moves with respect to the second weight balancing mechanism, the second driving structure may move the second weight in a direction opposite to a movement direction of the X-ray detector.

According yet a further aspect of the present disclosure, a method is provided. The method may include providing an X-ray imaging apparatus. The X-ray imaging apparatus may include an arm including a first end and a second end, a first X-ray component arranged at the first end of the arm, and a second X-ray component arranged at the second end of the arm. The first end may include a first weight balancing mechanism, and the first weight balancing mechanism may include a driving structure and a weight. The first X-ray component and the second X-ray component may be opposite to each other, and the first X-ray component may be configured to generate X-rays or receive X-rays. The method may further include moving the first X-ray component with respect to the first weight balancing mechanism. The method may further include moving, by the driving structure, the weight in a direction opposite to a direction of a movement of the first X-ray component with respect to the first weight balancing mechanism such that a center of gravity of the first end of the arm remains unchanged.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 11 is a flowchart illustrating an exemplary process for driving a first weight balancing mechanism according to some embodiments of the present disclosure.

DETAILED DESCRIPTION

Figure 1:
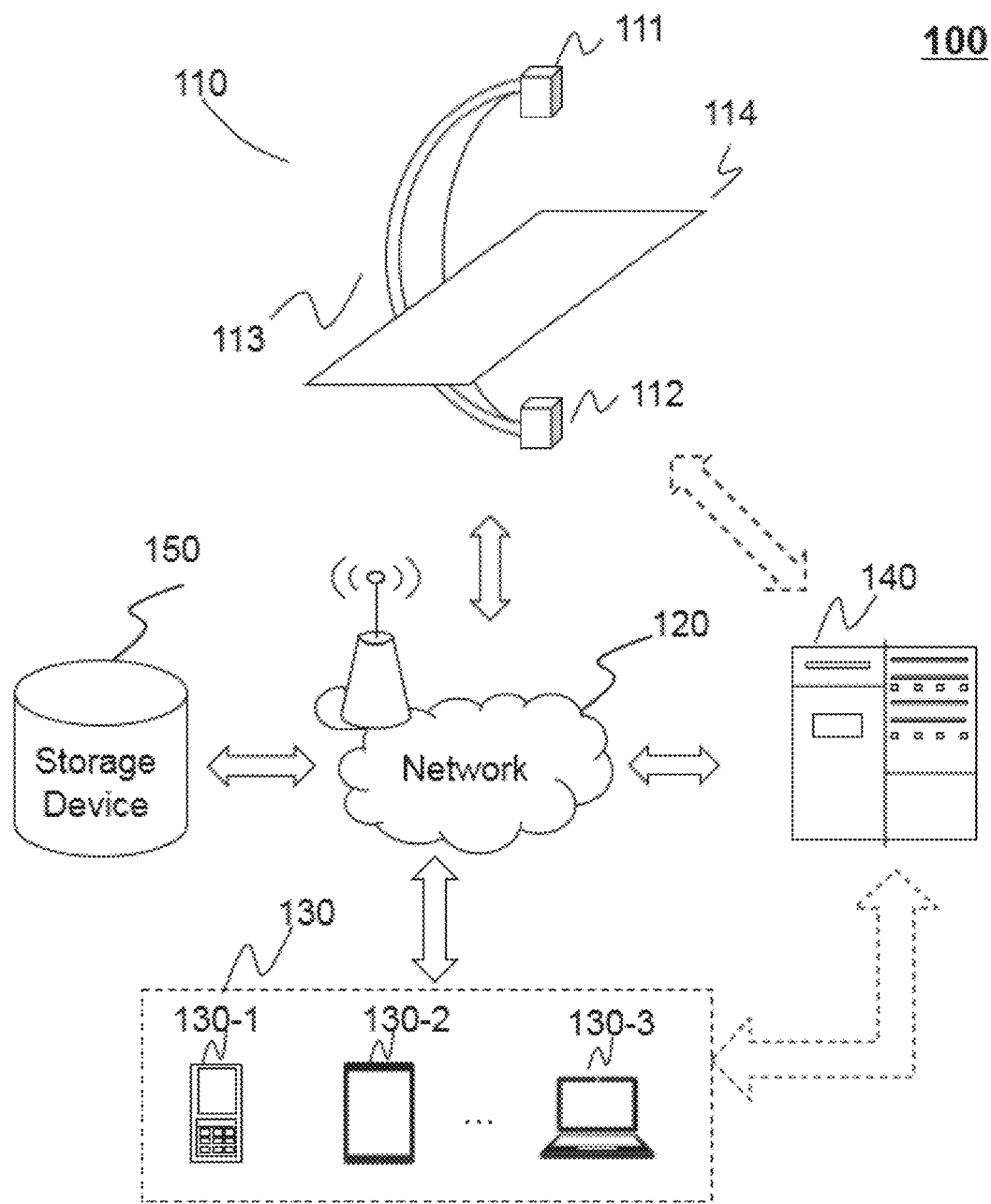
FIG. 1 is a schematic diagram illustrating an exemplary X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is to describe particular example embodiments only and is not intended to be limiting. As used herein, the singular forms "a," " " and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present application relates to an X-ray imaging apparatus. The X-ray imaging apparatus may include an arm, an X-ray tube, and an X-ray detector. The arm may include a first end and a second end. The X-ray tube may be configured to emit X-rays to an object, and the X-ray detector may be configured to receive the X-rays that pass through the object. In some embodiments, the X-ray tube may be placed at the second end, and the X-ray detector may be placed at the first end, vice versa. The X-ray tube and the X-ray detector may be opposite to each other. The first end may include a first weight balancing mechanism that includes a weight and a driving structure. When the X-ray detector moves with respect to the first weight balancing mechanism, the driving structure may drive the weight to move oppositely such that the center of gravity of the first end may remain unchanged. The source image distance (SID) of the X-ray imaging apparatus may change to a desired value by driving the X-ray detector, and because of the first weight balancing mechanism, the center of gravity of the first end does not change, which produce no or little tilt or rotation of the arm. The center of gravity of a body (e.g., the first end) may be a point at which the entire weight of the body may be considered as concentrated such that if the body is supported at this point, the body would remain in equilibrium in any position.

The following description is provided to help better understand the X-ray imaging apparatus. This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

FIG. 1 is a schematic diagram illustrating an exemplary X-ray imaging system according to some embodiments of the present disclosure. The X-ray imaging system 100 may include an X-ray imaging apparatus 110, a network 120, a terminal 130, a processing device 140, and a storage device 150. The components of the X-ray imaging system 100 may be connected to each other in various ways. Merely by way of example, the X-ray imaging apparatus 110 may be connected to the processing device 140 via the network 120. As another example, the X-ray imaging apparatus 110 may be connected to the processing device 140 directly or via the network 120. As a further example, the storage device 150 may be connected to the processing device 140 directly or via the network 120. As still a further example, the terminal 130 may be connected to the processing device 140 directly or via the network 120.

The X-ray imaging apparatus 110 may include an X-ray tube 111 (also referred to as an X-ray source), an X-ray detector 112, an arm 113, and a table 114. The arm 113 may be a C-shaped arm, a G-shaped arm, etc. The X-ray tube 111 and the X-ray detector 112 may be mounted on the arm 113. The arm 113 may include a first end and a second end. For example, the X-ray tube 111 may be mounted on the first end of the arm 113 and the X-ray detector 112 may be mounted on the second end of the arm 113. Alternatively, the X-ray tube 111 may be mounted on the second end of the arm 113 and the X-ray detector 112 may be mounted on the first end of the arm 113. The X-ray tube 111 and the X-ray detector 112 may be opposite to each other.

The table 114 may hold or support an object. The object may be a biological object (e.g., a patient, an animal) or a non-biological object (e.g., a man-made object). The X-ray tube 111 may emit X-rays to the object, and the X-rays may attenuate when passing through the object. The X-ray detector 112 may receive the attenuated X-rays that pass through the object and generate readings (also referred to as scanning data) corresponding to the received X-rays. In some embodiments, the X-ray detector 112 may include a scintillation detector (e.g., a cesium iodide detector), a gas detector, a circular detector, a square detector, an arcuate detector, or the like, or any combination thereof. The X-ray detector 112 may be a single-row detector or a multiple-row detector.

The network 120 may facilitate exchange of information and/or data. In some embodiments, one or more components of the X-ray imaging system 100 (e.g., the X-ray imaging apparatus 110, the terminal 130, the processing device 140, or the storage device 150) may send information and/or data to another component(s) in the X-ray imaging system 100 via the network 120. For example, the processing device 140 may obtain user instructions from the terminal 130 via the network 120. As another example, the processing device 140 may send instructions to the X-ray imaging apparatus 110 via the network 120. The instructions may control the X-ray tube 111 to emit X-rays or control the arm 113 to move to target positions according to the user instructions. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the X-ray imaging system 100 may be connected to the network 120 to exchange data and/or information.

The terminal 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 130 may remotely operate the X-ray imaging apparatus 110. In some embodiments, the terminal 130 may operate the X-ray imaging apparatus 110 via a wireless connection. In some embodiments, the terminal 130 may receive information and/or instructions inputted by a user, and send the received information and/or instructions to the X-ray imaging apparatus 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the X-ray imaging apparatus 110, the terminal 130, or the storage device 150. For example, the processing device 140 may obtain scanning data related to an object. The processing device 140 may further process the scanning data to generate an image of the object. As another example, the processing device 140 may obtain a current position and a target position of the arm 113 and calculate a required movement of the arm 113. The processing device 140 may further send instructions including the required movement to the arm 113 via the network 120 to move it to the target position.

The processing device 140 may include a central processing unit (CPU), a digital signal processor (DSP), a system on a chip (SoC), a microcontroller unit (MCU), or the like, or any combination thereof. In some embodiments, the processing device 140 may be a single server or a server group. The server group may be centralized or distributed. In some embodiments, the processing device 140 may be local or remote. For example, the processing device 140 may access information and/or data stored in the X-ray imaging apparatus 110, the terminal 130, and/or the storage device 150 via the network 120. As another example, the processing device 140 may be directly connected to the X-ray imaging apparatus 110, the terminal 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the X-ray imaging system 100 (e.g., the terminal 130, the processing device 140). One or more components of the X-ray imaging system 100 may access the data or instructions stored in the storage device 150 via the network 120. In some embodiments, the storage device 150 may be directly connected to or communicate with one or more components of the X-ray imaging system 100 (e.g., the terminal 130, the processing device 140). In some embodiments, the storage device 150 may be part of the processing device 140.

It should be noted that the above description of the X-ray imaging system 100 is provided for the purposes of illustration, and is not intended to limit the scope of the present disclosure. For persons having ordinary skills in the art, multiple variations and modifications may be made under the teachings of the present disclosure. However, those variations and modifications shall not depart from the scope of the present disclosure. For example, the X-ray imaging apparatus 110 may be modified and employed in another kind of medical imaging system, including but not limited to a PET (Positron Emission Tomography) system, a SPECT (Single Photon Emission Computed Tomography) system, a CT (Computed Tomography) system, an MRI (Magnetic Resonance Imaging) system, a DR (digital radiography) system, a PET-CT system, a PET-MRI system, or a SPECT-MRI system. Merely by way of example, the X-ray tube 111 and the X-ray detector 112 of the X-ray imaging apparatus 110 may be replaced by a transmitting coil and a receiving coil, and the X-ray imaging apparatus 110 may be employed in an MRI system.

Figure 2:
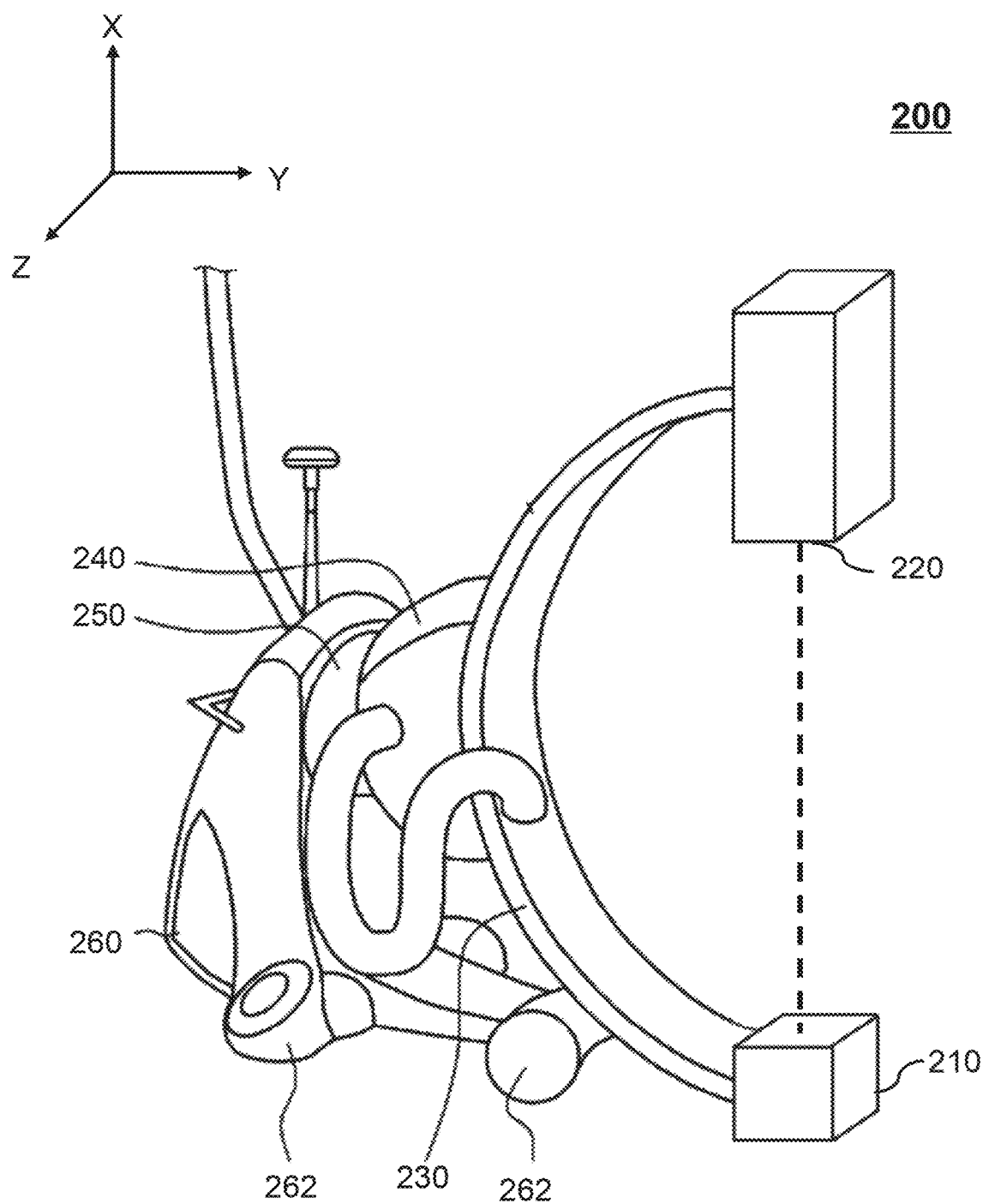
FIG. 2 is a schematic diagram illustrating an exemplary X-ray imaging apparatus according to some embodiments of the present disclosure.

FIG. 2 is a schematic diagram illustrating an exemplary X-ray imaging apparatus according to some embodiments of the present disclosure. The X-ray imaging apparatus 200 may be an example of the X-ray imaging apparatus 110. The X-ray imaging apparatus 200 may include an X-ray tube 210, an X-ray detector 220, an arm 230, a supporting structure 240, a vertical component 250, and a base component 260. The X-ray tube 210 may be an example of the X-ray tube 111. The X-ray tube 210 may be configured to emit X-rays. The X-ray detector 220 may be an example of the X-ray detector 112. The X-ray detector 220 may receive the X-rays that pass through the object and generate readings (also referred to as scanning data) corresponding to the received X-rays.

As shown in FIG. 2, the arm 230 may be a C-shaped arm or a G-shaped arm. The arm 230 may include two ends (e.g., a first end and a second end). The X-ray tube 210 and the X-ray detector 220 may be mounted on the two ends of the arm 230, respectively. The X-ray tube 210 and the X-ray detector 220 may be opposite to each other. The arm 230 may be hinge-connected to the supporting structure 240, and the supporting structure 240 may be hinge-connected to the vertical component 250. The supporting structure 240 and the vertical component 250 may enable the arm 230 to move freely in three dimensions (e.g., X-direction, Y-direction, and Z-direction). In some embodiments, the arm 230, the supporting structure 240 and/or the vertical component 250 may be integrated into a structure. The vertical component 250 may be installed on the base component 266. The base component 260 may include a plurality of wheels 262, and the X-ray imaging apparatus may move freely via the plurality of wheels 262.

The X-ray imaging apparatus 200 may be configured to scan an object. In some embodiments, the arm 230 may be adjusted to an initial scan position before the scan of the object. Merely by way of example, the X-ray tube 210 and the X-ray detector 220 may be vertical in the initial scan position. In some embodiments, a line connecting the X-ray tube 210 and the X-ray detector 220 (which is also the path of central emitted X-rays) may pass through the object (e.g., a region of interest (ROI) of the object). In some embodiments, the arm 230 may rotate around the object while maintaining the X-rays passing through the object or the ROI thereof to generate a plurality of readings (also referred to as scanning data) on the X-ray detector 220. The scanning data may first be reconstructed to generate a plurality of images corresponding to different sections of the object in different angles (e.g., different slices of the object). The processing device 140 may generate a 3D image of the object based on the plurality of images.

The distance between an X-ray tube (e.g., the X-ray tube 210) and an X-ray detector (e.g., the X-ray detector 220) may be referred to as a source imaging distance (SID). The SID of the X-ray imaging apparatus 200 may affect size, resolution and/or quality of the reconstructed image, and may be adjusted according to parameters related to the object. The parameters related to the object may include specifics of the object (e.g., gender, height, weight), a section of the object to be scanned (e.g., a head, a chest), etc.

Figure 3:
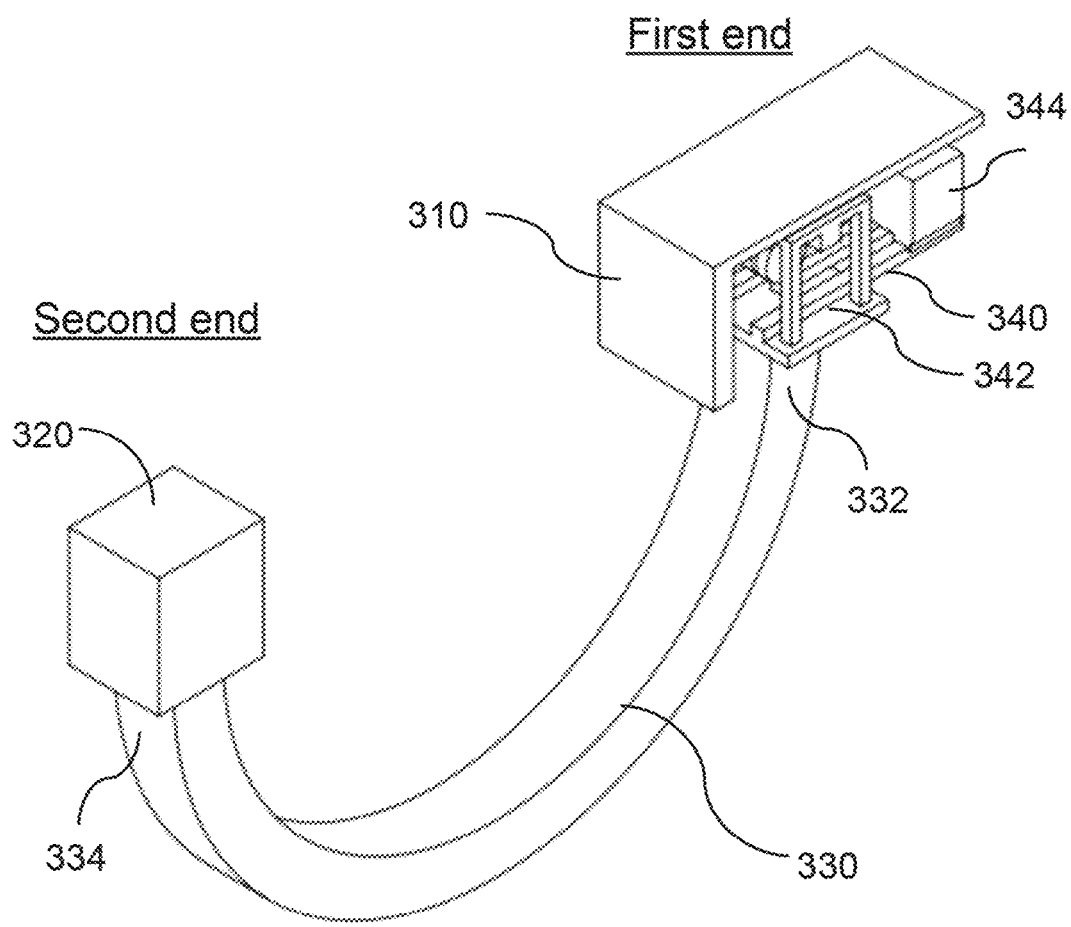
FIG. 3 is a schematic diagram illustrating an exemplary X-ray imaging apparatus according to some embodiments of the present disclosure.

FIG. 3 is a schematic diagram illustrating an exemplary X-ray imaging apparatus according to some embodiments of the present disclosure. The X-ray imaging apparatus 300 may be an example of the X-ray imaging apparatus 110. As shown in FIG. 3, the X-ray imaging apparatus 300 may include a first X-ray component 310, a second X-ray component 320, and an arm 330. In some embodiments, the first X-ray component 310 may include an X-ray detector, and the second X-ray component 320 may include an X-ray tube. Alternatively, the first X-ray component may include an X-ray tube, and the second X-ray component may include an X-ray detector. The X-ray tube may be configured to generate X-rays. The X-ray detector may be configured to receive at least part of the X-rays generated by the X-ray tube. The arm 330 may include a first end 332, and a second end 334. The first end 332 may include a first weight balancing mechanism 340. The first X-ray component 310 may be mounted on the first weight balancing mechanism 340 and may move relative to it. The second X-ray component 320 may be directly mounted on the second end 334. The first X-ray component 310 and the second X-ray component 320 may be opposite to each other. The first X-ray component 310 may move in the direction toward or away from the second end 334 of the arm 330, and such movement may cause the change of the SID. In some embodiments, the movement of the first X-ray component 310 may cause a change of the center of gravity of the first end 332, and the first weight balancing mechanism 340 may compensate the change of the center of gravity of the first end 332 and maintain the center of gravity of the first end 332 unchanged. For example, the first weight balancing mechanism 340 may include a driving structure 342 and a weight 344. When the first X-ray component 310 moves, the driving structure 342 may drive the weight 344 to move in the direction opposite to the movement of the first X-ray component 310. The driving structure 342 may be a gear structure (as shown as 600 in FIG. 6A, and 620 in FIG. 6B), a lead screw structure (as shown as 734 in FIG. 7), a magnetism structure (as shown as 832 in FIG. 8), a tensile structure (as shown as 932 in FIG. 9), etc. Details regarding the structure of the first weight balancing mechanism 340 may be found elsewhere in the present disclosure (e.g., FIGS. 4A to 9, and the descriptions thereof).

It should be noted that the descriptions of the X-ray imaging apparatus 300 herein is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, the second end 334 may include a second weight balancing mechanism mounted on it. The second X-ray component 320 may be mounted on the second weight balancing mechanism (not shown) and may move relative to the second weight balancing mechanism. The second X-ray component 320 may move in the direction toward or away the first end 332 of the arm 330, and such movement may cause the SID to change. In some embodiments, the movement of the second X-ray component 320 may cause a change of the center of gravity of the second end 334, and the second weight balancing mechanism may compensate the change of the center of gravity of the second end 334 and maintain the center of gravity of the second end 334 unchanged.

Figure 4A:
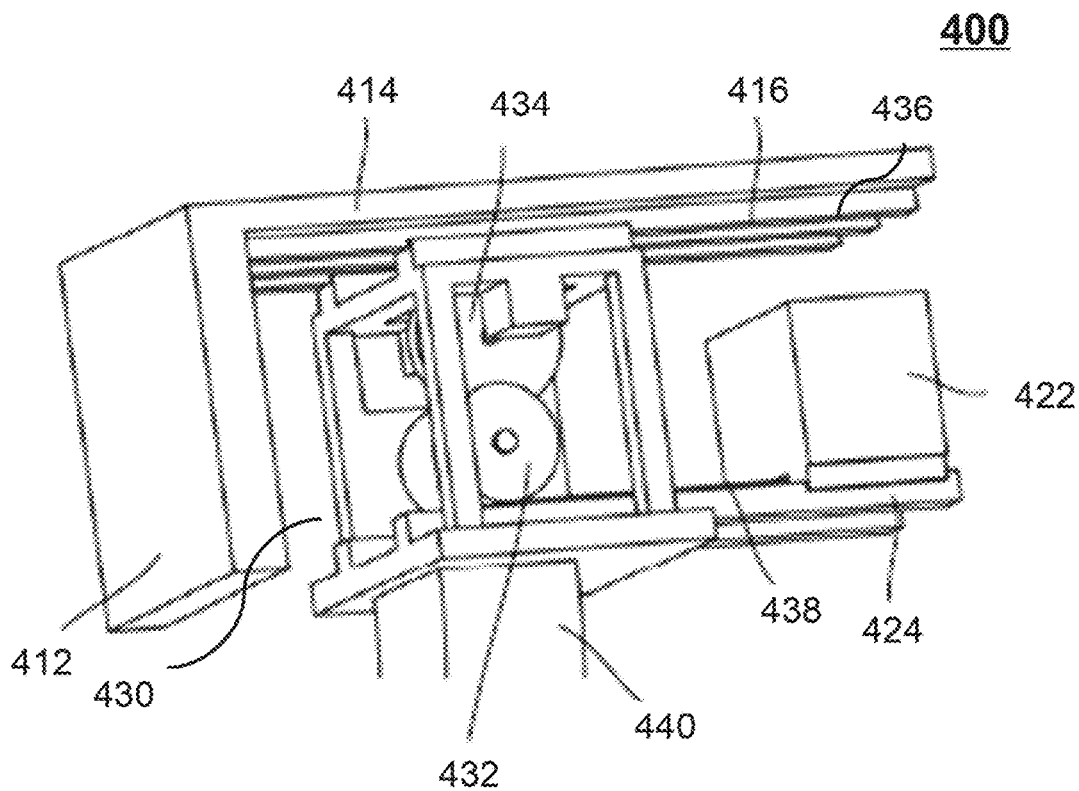
FIG. 4A shows a perspective view of an exemplary first weight balancing mechanism according to some embodiments of the present disclosure.
Figure 4B:
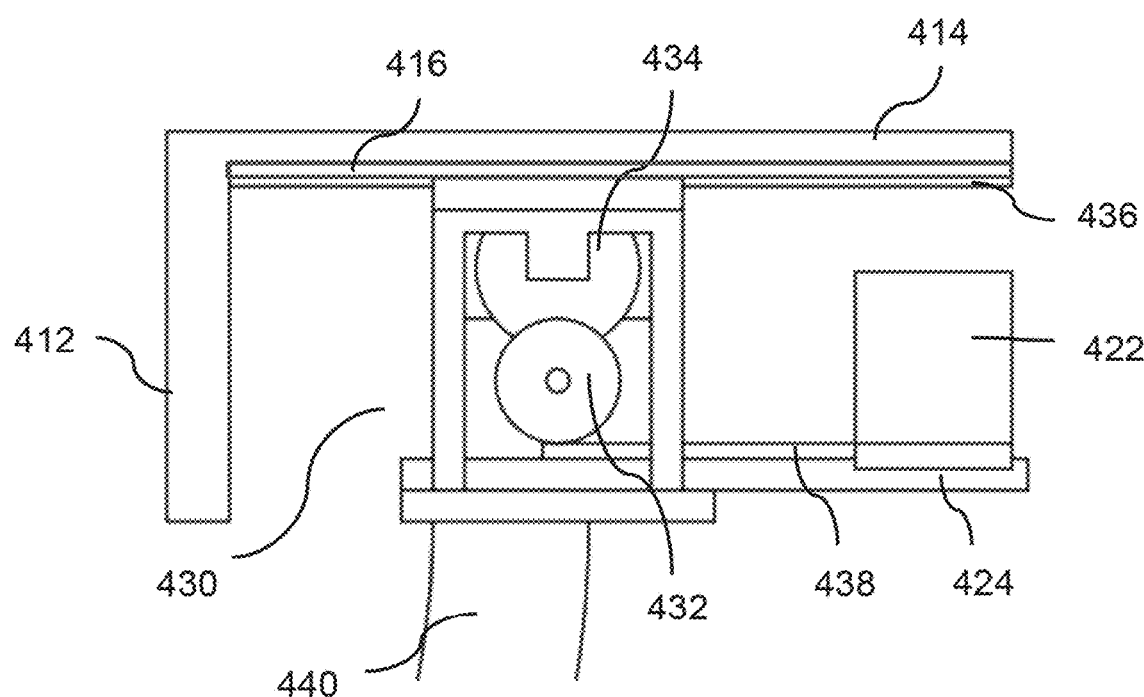
FIG. 4B shows a side view of an exemplary first weight balancing mechanism according to some embodiments of the present disclosure.

FIG. 4A shows a perspective view of an exemplary first weight balancing mechanism according to some embodiments of the present disclosure. A side view of the first weight balancing mechanism is shown in FIG. 4B. As shown in FIGS. 4A and 4B, first weight balancing mechanism 400 may include a weight 422 and a driving structure 430. The first weight balancing mechanism 400 may be an example of the first weight balancing mechanism 340. The driving structure 430 may be an example of the driving structure 342. The driving structure 430 may include a motor 432, a gear 434, a first transmission part 436, and a second transmission part 438. The first weight balancing mechanism 400 may be connected to a first end 440 of an arm (e.g., the arm 113, the arm 230, the arm 330). An X-ray detector 412 may be connected to a first fixing component 414. The first fixing component 414 may be connected to a guiding rail 416. The first fixing component 414 and the X-ray detector 412 may move on the guiding rail 416. The weight 422 may be connected to a second fixing component 424. The gear 434 may engage with the first transmission part 436 and the second transmission part 438. The first transmission part 436 may be connected to the first fixing component 414. The second transmission part 438 may be connected to the second fixing component 424. In some embodiments, the gear 434 may include one or more gears or a gearbox. In some embodiments, the gears may engage with each other, or be connected via belts or chains. The first transmission part 436 and the second transmission part 438 may each include one or more gears, one or more racks, or the like, or any combination thereof. The second transmission part 438 may be same as or different from the first transmission part 436. For example, the first transmission part 436 and the second transmission part 438 may each include a rack (as shown as 600 in FIG. 6A). As another example, the first transmission part 436 and the second transmission part 438 may each include a rack and a gear (as shown as 620 in FIG. 6B). As yet a further example, the first transmission part 436 may include a rack and a gear, and the second transmission part 438 may include a rack and three gears.

In some embodiments, the driving structure 430 (including the gear 434, the first transmission part 436 and the second transmission part 438) may include an odd number of total gears to ensure that the movement direction of the X-ray detector 412 is opposite to the movement direction of the weight 422. When the X-ray detector 412 moves with respect to the first weight balancing mechanism 400, the driving structure 430 may move the weight 422 oppositely such that the first weight balancing mechanism 400 maintains the center of gravity of the first end 440 unchanged. Details regarding the center of gravity of the first end 440 before and after the movement may be found elsewhere in the present disclosure (e.g., FIGS. 5A and 5B, and the descriptions thereof). In some embodiments, the weight of the weight 422 may be the same as or different from the weight of the X-ray detector 412.

In some embodiments, the driving structure 430 may receive an instruction from other component(s) of the X-ray imaging system 100 (e.g., the terminal 130, the processing device 140). The instruction may be related to a distance that the X-ray detector 412 needs to move in order to satisfy a specific SID. In some embodiments, the specific SID may be determined by the processing device 140 based on parameters related to the object. The parameters related to the object may include specifics of the object (e.g., gender, height, weight), a section of the object to be scanned (e.g., a head, a chest), etc. In some embodiments, the specific SID may be selected from a plurality of candidate SIDs based on the parameters related to the object. The plurality of candidate SIDs may be pre-stored in the storage device 150 or a cloud-based storage in the network 120. The parameters related to the object may be manually input by a user via the terminal 130 or may be automatically determined by a plurality of sensors in the X-ray imaging system 100 (not shown in the figure). In some embodiments, the user may input the specific SID directly based on his/her experience. In response to the instruction, the motor 432 may drive the gear 434 to rotate. The gear 434 may drive the first transmission part 436 to move the X-ray detector 412 and the first fixing component 414. The movement of the X-ray detector 412 may cause a change of the SID of the X-ray imaging apparatus 300. The motor 432 may drive the gear 434 until the specific SID of the X-ray imaging apparatus 300 is met. At the same time, the gear 434 may drive the second transmission part 438 to move the weight 422 and the second fixing component 424. The weight 422 may move in a direction opposite to the direction of the movement of the X-ray detector 412 to compensate the change of the center of gravity of the first end 440 caused by the movement of the X-ray detector 412.

In some embodiments, a user may turn on the power of the motor 432, and the motor 432 may drive the gear 434 to rotate, driving the X-ray detector 412 and the weight 422 to move. When a specific SID is satisfied, the user may turn off the power of the motor 432. Alternatively or additionally, a user may pull or push the X-ray detector 412 manually to meet a desired SID, and the driving structure 430 may move the weight 422 accordingly. Alternatively, the user may pull or push the weight 422 manually, and the driving structure 430 may move the X-ray detector 412 to satisfy a desired SID.

In some embodiments, a computing device (e.g., the processing device 140, the terminal 130) may generate a desired SID based on certain preset rules or regulations and the information of the object. The computing device may also determine a current position of the X-ray detector 412 and a target position of the X-ray detector 412 based on the desired SID. The computing device may also determine the movement of the X-ray detector 412 to the target position to meet the desired SID. The computing device may then generate and send instructions of rotation time and/or rotation speed based on the movement of the X-ray detector 412 to the motor 432 to move the X-ray detector 412 to the target position so that the desired SID may be satisfied.

Figure 5A:
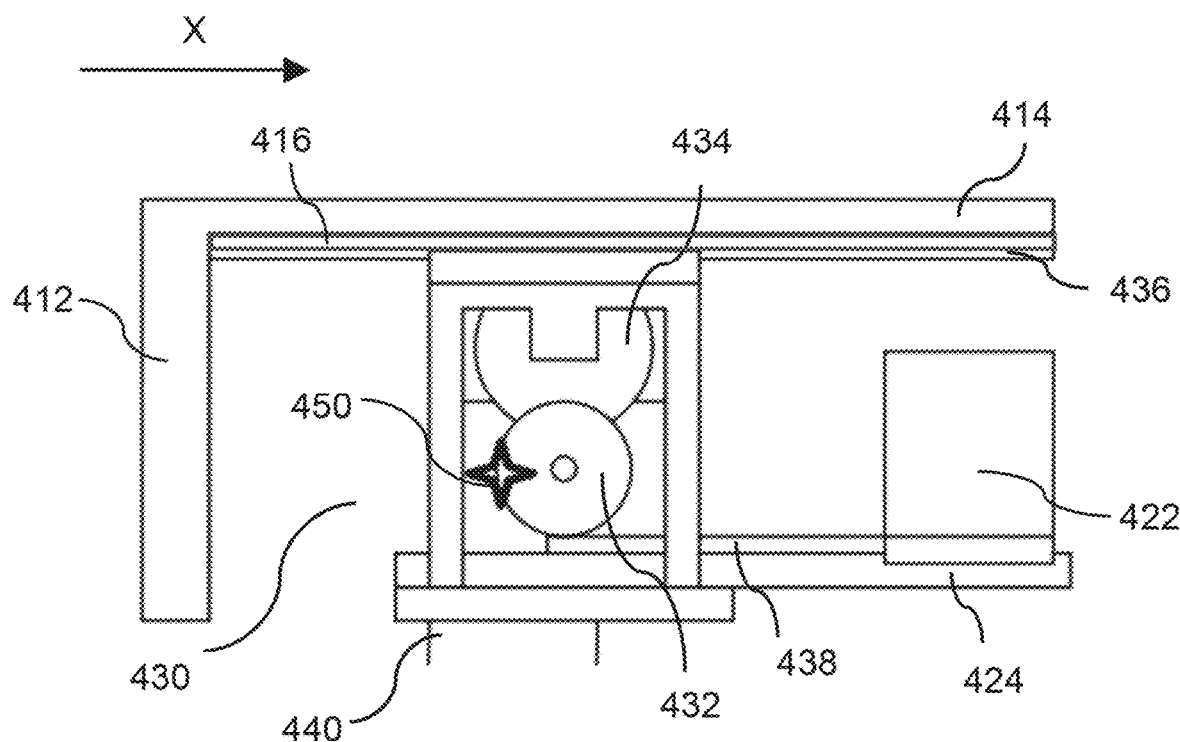
FIG. 5A shows an exemplary first weight balancing mechanism when an X-ray apparatus is in a first configuration according to some embodiments of the present disclosure.
Figure 5B:
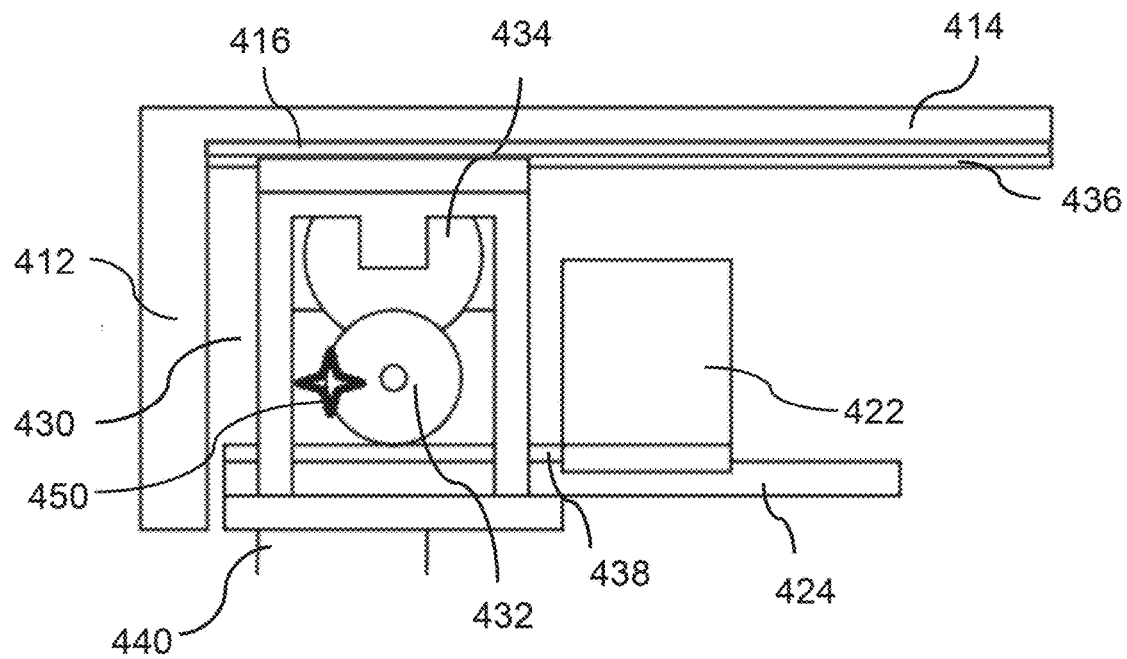
FIG. 5B shows an exemplary first weight balancing mechanism when an X-ray apparatus is in a second configuration according to some embodiments of the present disclosure.

FIG. 5A shows an exemplary first weight balancing mechanism when the X-ray apparatus is in a first configuration according to some embodiments of the present disclosure. The first configuration of the X-ray imaging apparatus 300 may correspond to a first SID (or referred to as an initial SID). FIG. 5B shows the exemplary first weight balancing mechanism when the X-ray apparatus is in a second configuration according to some embodiments of the present disclosure. The second configuration of the X-ray imaging apparatus 300 may correspond to a second SID (or a desired SID). In order to satisfy the second SID, the X-ray detector 412 may move in a forward direction of X-axis. The weight 422 may move in a backward direction of X-axis. In some embodiments, the X-ray detector 412 and the weight 422 may be driven to move under the action of a motor (e.g., the motor 432), or may be manually driven by a user to move. As shown in FIGS. 5A and 5B, the center of gravity 450 of the first end 440 may be unchanged when the X-ray apparatus changes from the first configuration to the second configuration.

Figure 6A:
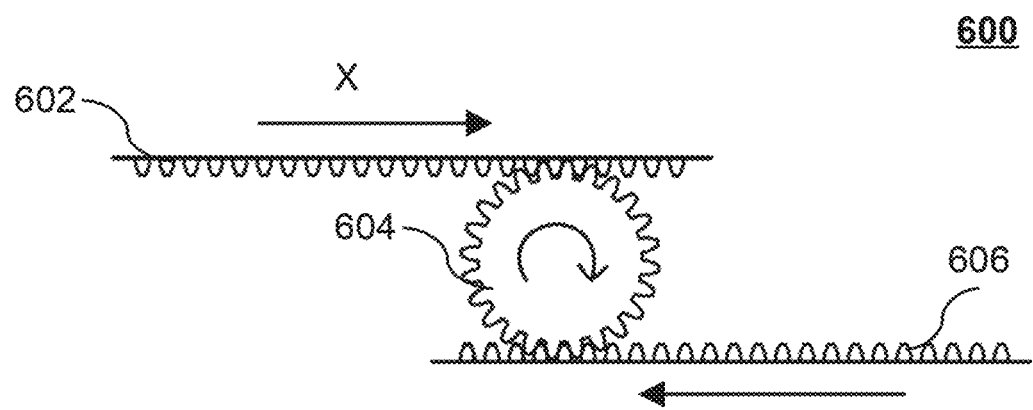
FIGS. 6A and 6B show two exemplary driving structures according to some embodiments of the present disclosure.
Figure 6B:
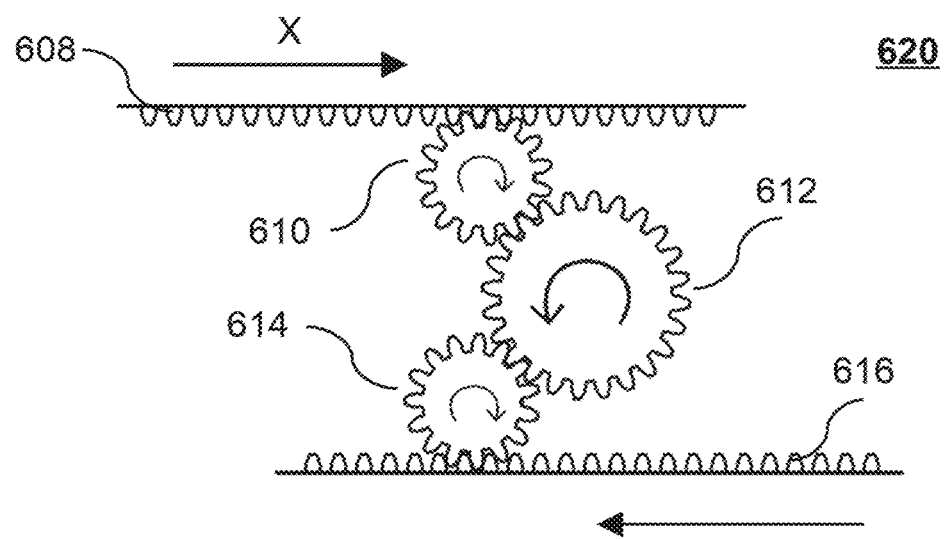

FIGS. 6A and 6B show two exemplary driving structures according to some embodiments of the present disclosure. The driving structures 600 and 620 may be two examples of the driving structure 430. As shown in FIG. 6A, the driving structure 600 may include a first transmission part (e.g., a first rack 602), a gear 604, and a second transmission part (e.g., a second rack 606). The gear 604 may engage with the first rack 602 and the second rack 606. As shown in FIG. 6A, the first rack 602 may move in the forward direction of X-axis, the gear 604 may rotate clockwise, and the second rack 606 may move in the backward direction of X-axis. In some embodiments, the gear 604 may be driven to rotate clockwise, driving the first rack 602 and the second rack 606 to move simultaneously. In some embodiments, the first rack 602 may be driven to move in the forward direction of X-axis, driving the gear 604 to rotate clockwise. The gear 604 may further drive the second rack 606 to move. In some embodiments, the second rack 606 may be driven to move in the backward direction of X-axis, driving the gear 604 to rotate clockwise. The gear 604 may further drive the first rack 602 to move. The driving structure 600 (e.g., the first rack 602, the gear 604, the second rack 606) may be driven by a motor (e.g., the motor 432) or a user. It should be noted that the movement direction and/or the rotation direction is merely for the purposes of illustration and is not intended to limit the scope of the present disclosure. In some embodiments, the second rack 606 may move in the forward direction of X-axis, the first rack 602 may move in the backward direction of X-axis, and the gear 604 may rotate counterclockwise.

As shown in FIG. 6B, the driving structure 620 may include a first rack 608, a first gear 610, a second gear 612, a third gear 614, and a second rack 616. In some embodiments, the first rack 608 and the first gear 610 may be referred to herein as the first transmission part, and the second rack 616 and the third gear 614 may be referred to herein as the second transmission part.

The second gear 612 may engage with the first gear 610 and the third gear 614. The first gear 610 may engage with the first rack 608, and the third gear 614 may engage with the second rack 616. As shown in FIG. 6B, the first rack 608 may move in the forward direction of X-axis, the second rack 616 may move in the backward direction of X-axis. The first gear 610 and the third gear 614 may rotate clockwise, and the second gear 612 may rotate counterclockwise. It should be noted that the movement direction and/or the rotation direction is merely for the purposes of illustration and is not intended to limit the scope of the present disclosure. In some embodiments, the driving structure may include any suitable odd number of gears (besides one and three as illustrated in the driving structures 600 and 620) to such that the movement direction of the first rack (which is connected to the X-ray detector 412) is opposite to the movement direction of the second rack (which is connected to the weight 422).

Figure 7:
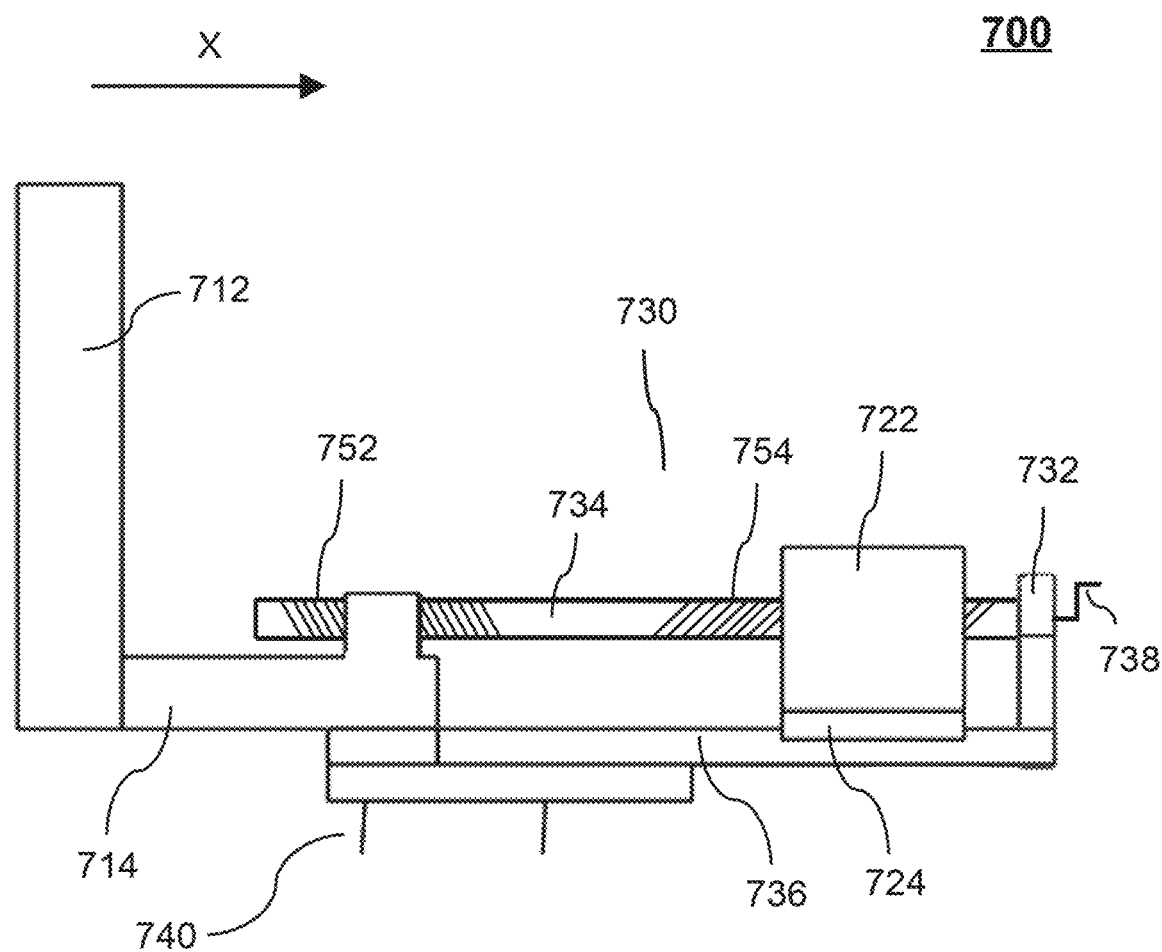
FIG. 7 is a schematic diagram illustrating an exemplary first weight balancing mechanism according to some embodiments of the present disclosure.

FIG. 7 is a schematic diagram illustrating an exemplary first weight balancing mechanism according to some embodiments of the present disclosure. As shown in FIG. 7, first weight balancing mechanism 700 may include a weight 722, and a driving structure 730. The first weight balancing mechanism 700 may be an example of first weight balancing mechanism 340. The driving structure 730 may be an example of the driving structure 342. The driving structure 730 may include a transmission component 732, a lead screw 734, and a handle 738. The first weight balancing mechanism 700 may be connected to a first end 740 of an arm (e.g., the arm 113, the arm 230, the arm 330). An X-ray detector 712 may be connected to a first fixing component 714. The first fixing component 714 may be connected to a guiding rail 736. The X-ray detector 712 and the first fixing component 714 may move on the guiding rail 736. The weight 722 may be connected to a second fixing component 724, and the second fixing component 724 may be connected to the guiding rail 736. The weight 722 and the second fixing component 724 may move on the guiding rail 736.

The lead screw 734 may include a first part 752 and a second part 754. The handedness of threads of the first part 752 of the lead screw 734 may be different from the handedness of threads of the second part 754 of the lead screw 734. The first fixing component 714 may include inner threads matching the threads of the first part 752 of the lead screw 734. The first part 752 of the lead screw 734 may be connected to the first fixing component 714. In some embodiments, the first fixing component 714 may be omitted, and the first part 752 of the lead screw 734 may be directly connected to the X-ray detector 712. Alternatively, the first fixing component 714 may be integrated with the X-ray detector 712, and the first part 752 of the lead screw 734 may be connected to the integrated structure. The weight 722 or the second fixing component 724 may include inner threads matching the threads of the second part 754 of the lead screw 734. The second part 754 of the lead screw 734 may be connected to the weight 722.

In some embodiments, the weights of the weight 722 and the X-ray detector may have a certain ratio. The thread pitches of the threads of the first part 752 and the second part 754 may satisfy a relationship associated with the ratio. The relationship between the first part 752 and the second part 754 associated with the ratio may help to maintain the center of gravity of the first end 740 unchanged when the X-ray detector 712 and the weight 722 moves. For example, if the weight 722 has the same weight as the X-ray detector 712, the thread pitches of the threads of the second part 754 may be same as the thread pitches of the threads of the first part 752 (but with opposite handedness).

In some embodiments, the driving structure 730 may further include a motor (not shown in the figure). The motor may receive an instruction from other component(s) of the X-ray imaging system 100 (e.g., the terminal 130, the processing device 140). The instruction may be related to a distance that the X-ray detector 712 needs to move in order to satisfy a specific SID. In some embodiments, the specific SID may be determined by the processing device 140 based on parameters related to the object. The parameters related to the object may include specifics of the object (e.g., gender, height, weight), a section of the object to be scanned (e.g., a head, a chest), etc. In some embodiments, the specific SID may be selected from a plurality of candidate SIDS based on the parameters related to the object. The plurality of candidate SIDS may be pre-stored in the storage device 150 or a cloud-based storage in the network 120. The parameters related to the object may be manually input by a user via the terminal 130 or may be automatically determined by a plurality of sensors in the X-ray imaging system 100 (not shown in the figure). In some embodiments, the user may input the specific SID directly based on his/her experience. In response to the instruction, the motor may transmit a torque by the transmission component 732 to drive the lead screw 734 to rotate. When the lead screw 734 rotates, the X-ray detector 712 and the first fixing component 714 may be driven to move. The X-ray detector 712 may move in the direction of toward or away a second end of the arm. As shown in FIG. 7, the X-ray detector 712 may move in the forward direction of X-axis. The movement of the X-ray detector 712 may cause the change of the SID of the X-ray imaging apparatus 300. The motor may drive the lead screw 734 until the specific SID of the X-ray imaging apparatus 300 is satisfied. At the same time, the lead screw 734 may drive the weight 722 to move. The weight 722 may move in the backward direction of X-axis such that the center of gravity of the first end may be unchanged. It should be noted that the movement direction is merely for the purposes of illustration, and is not intended to limit the scope of the present disclosure. In some embodiments, the X-ray detector 712 may move in the backward direction of X-axis, and the weight may move in the forward direction of X-axis.

In some embodiments, a user may turn on the power of the motor, and the motor may drive the lead screw 734 to rotate, driving the X-ray detector 712 and the weight 722 to move. The user may turn off the power of the motor when a specific SID is satisfied. Alternatively or additionally, the X-ray detector 712 may be manually by a user moved to meet the desired SID. For example, a user may rotate the handle 738 to drive the lead screw 734, driving the X-ray detector 712 and the weight 722 to move. In some embodiments, a computing device (e.g., the processing device 140, the terminal 130) may generate a desired SID based on certain preset rules or regulations and the information of the object. The computing may also determine a current position of the X-ray detector 712 and a target position of the X-ray detector 712 based on the desired SID. The computing device may determine the movement of the X-ray detector 712 to the target position to meet the desired SID. The computing device may then generate and send instructions of rotation time and/or rotation speed based on the movement of the X-ray detector 712 to the driving structure 730 to move the X-ray detector 712 to the target position so that the desired SID may be satisfied.

Figure 8:
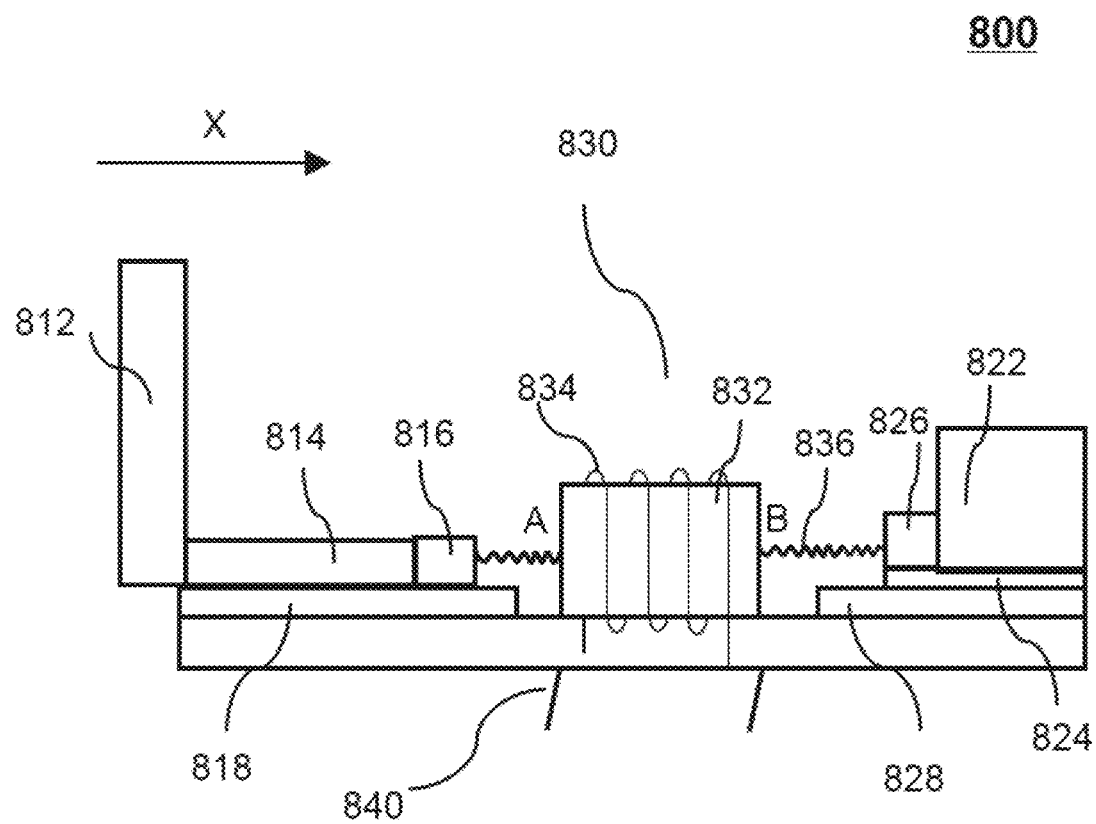
FIG. 8 is a schematic diagram illustrating an exemplary first weight balancing mechanism according to some embodiments of the present disclosure.

FIG. 8 is a schematic diagram illustrating an exemplary first weight balancing mechanism according to some embodiments of the present disclosure. As shown in FIG. 8, first weight balancing mechanism may include a weight 822, and a driving structure 830. The first weight balancing mechanism 800 may be an example of the first weight balancing mechanism 340. The driving structure 830 may be an example of the driving structure 342. The driving structure 830 may include a first magnet 816, a second magnet 826, an electromagnet 832, and an electric circuit supplying electric power to the electromagnet 832 (not shown in the figure). The first weight balancing mechanism 800 may be connected to a first end 840 of an arm (e.g., the arm 113, the arm 230, the arm 330). A first fixing component 814 may be connected to an X-ray detector 812 and a first magnet 816. The X-ray detector 812 and the first fixing component 814 may move on the first guiding rail 818. A second fixing component 824 may be connected to the weight 822 and a second magnet 826. The weight 822 and the second fixing component 824 may move on the second guiding rail 828. The first magnet 816 and the second magnet 826 may be electromagnets or permanent magnets. The electromagnet 832 may be coiled by connecting wires 834. In some embodiments, the magnetic field intensity of the electromagnet 832 may be changed (e.g., increased, decreased) by adjusting the current in the connecting wires 834. The current may be adjusted by changing voltage and/or resistance in the electric circuit that supplies electric power to the connecting wires 834.

The electromagnet 832 may be physically connected to the first magnet 816 and the second magnet 826 via springs 836. The first end A of the electromagnet 832 and the first magnet 816 may have the same polarity and may repel each other. The second end B of the electromagnet 832 and the second magnet 826 may have the same polarity and may repel each other. In some embodiments, the repulsive force between the electromagnet 832 and the first magnet 816 may be the same as or different from the repulsive force between the electromagnet 832 and the second magnet 826. The repulsive force between the electromagnet 832 and the first magnet 816 (or the second magnet 826) may be determined based on the distance therebetween and their magnetic field intensities.

In some embodiments, the driving structure 830 may receive an instruction from other component(s) of the X-ray imaging system 100 (e.g., the terminal 130, the processing device 140). The instruction may be related to a distance that the X-ray detector 812 needs to move in order to satisfy a specific SID. In response to the instruction, the current in the connecting wire 834 may be adjusted by changing voltage and/or resistance in the electric circuit supplying electric power to the electromagnet 832 (not shown in the figure) and change the magnetic field intensity of the electromagnet 832. In some embodiments, the voltage and/or the resistance may be changed by a user. For example, the resistance may be a variable resistance. When the magnetic field intensity of the electromagnet 832 changes, the repulsive force (or the attractive force) between the first magnet 816 and the electromagnet 832 may change, driving the X-ray detector 812 and the first fixing component 814 to move on the first guiding rail 818. At the same time, the repulsive force (or the attractive force) between the second magnet 826 and the electromagnet 832 may also change, driving the weight 822 and the second fixing component 824 to move on the second guiding rail 828. The weight 822 may move in a direction opposite to the direction of the movement of the X-ray detector 812.

Under the condition that the first end A of the electromagnet 832 and the first magnet 816 have the same polarity and the second end B of the electromagnet 832 and the second magnet 826 have the same polarity, if the magnetic field intensity of the electromagnet 832 is increased, the X-ray detector 812 may move in the backward direction of X-axis, and the weight 822 may move in the forward direction of X-axis. If the magnetic field intensity of the electromagnet 832 is decreased, the springs 836 may drag the X-ray detector 812 to move in a forward direction of X-axis, and the weight 822 to move in a backward direction of X-axis.

Under the condition that the first end A of the electromagnet 832 and the first magnet 816 have different polarities and the second end B of the electromagnet 832 and the second magnet 826 have different polarities, if the magnetic field intensity of the electromagnet 832 is increased, the X-ray detector 812 may move in the forward direction of X-axis and the weight 822 may move in the backward direction of X-axis. If the magnet field intensity of the electromagnet 832 is decreased, the springs 836 may push the X-ray detector 812 to move in a backward direction of X-axis, and the weight 822 to move in a forward direction of X-axis.

In some embodiments a computing device (e.g., the processing device 140, the terminal 130) may generate a desired SID based on certain preset rules or regulations and the information of the object. The computing device may also determine a current position of the X-ray detector 812 and a target position of the X-ray detector 812 based on the desired SID. The computing device may also determine the movement of the X-ray detector 812 to the target position to meet the desired SID. The computing device may then generate and send instructions of rotation time and/or rotation speed based on the movement of the X-ray detector 812 to the driving structure 830 to move the X-ray detector 812 to the target position so that the desired SID may be satisfied.

Figure 9:
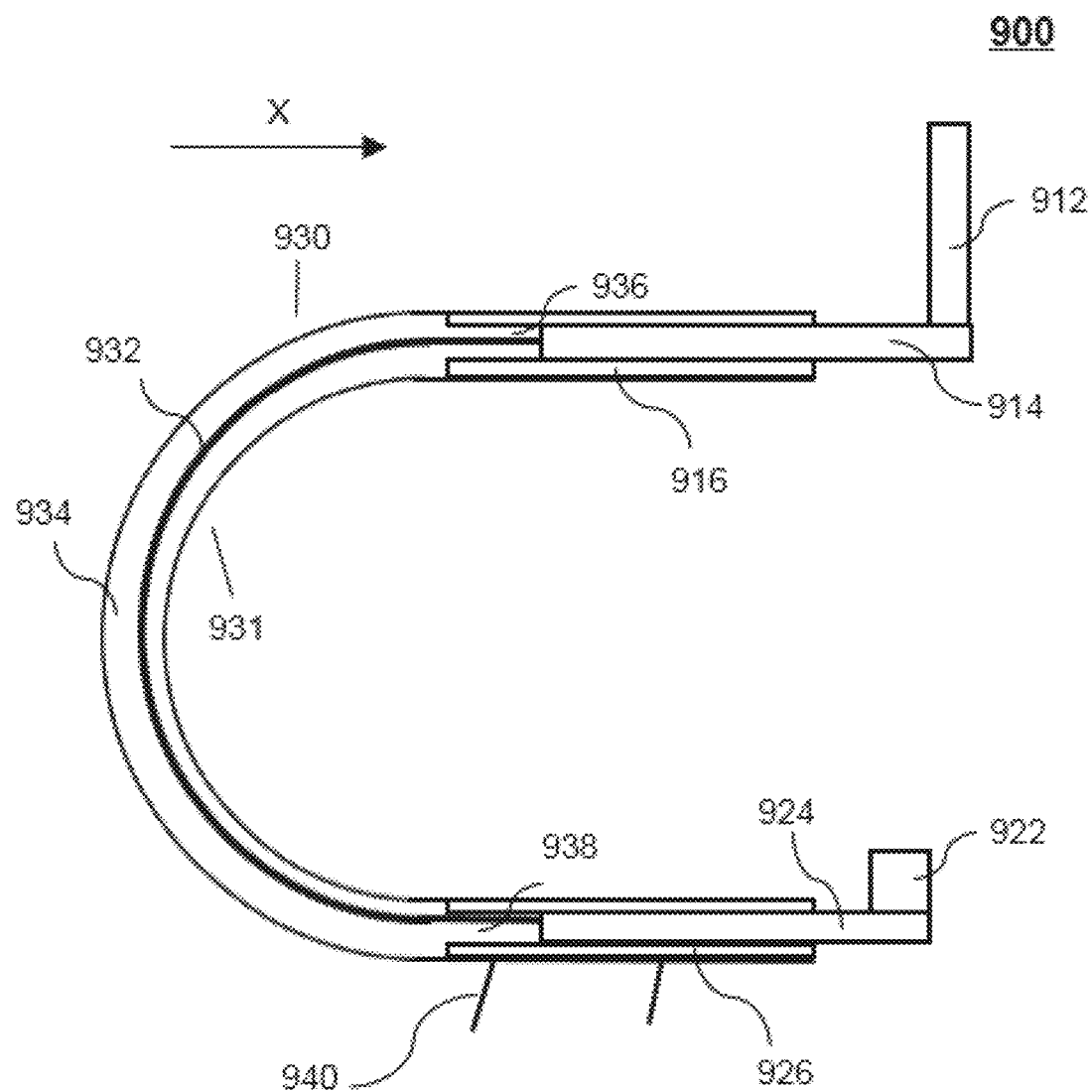
FIG. 9 is a schematic diagram illustrating an exemplary first weight balancing mechanism according to some embodiments of the present disclosure.

FIG. 9 is a schematic diagram illustrating an exemplary first weight balancing mechanism according to some embodiments of the present disclosure. As shown in FIG. 9, first weight balancing mechanism 900 may include a weight 922 and a driving structure 930. The first weight balancing mechanism 900 may be an example of the first weight balancing mechanism 340. The driving structure 930 may be an example of the driving structure 342. The driving structure 930 may include a tube 931, a cable 932, a first guiding rail 916 and a second guiding rail 926. The first weight balancing mechanism 900 may be connected to the first end 940 of an arm (e.g., the arm 113, the arm 230, the arm 330). An X-ray detector 912 may be connected to a first fixing component 914. The first fixing component 914 may be placed in the first guiding rail 916. In some embodiments, the first guiding rail 916 may have a high frictional force (e.g., made of a material with high friction) that prevent the first fixing component 914 and the X-ray detector 912 from sliding on the first guiding rail 916 when they are not driven to move (even if the arm is tilted). The weight 922 may be connected to a second fixing component 924. The second fixing component 924 may be placed in the second guiding rail 926. In some embodiments, the second guiding rail 926 may have a high frictional force (e.g., made of a material with high friction) that prevent the second fixing component 924 and the weight 922 from sliding on the second guiding rail 926 when they are not driven to move (even if the arm is tilted). In some embodiments, the first guiding rail 916 and the second guiding rail 926 may be made with the same material or different materials. The tube 931 may include a curved section 934, a first straight section 936, and a second straight section 938. The cable 932 may be placed in the curved section 934 of the tube 931 and connected to the first fixing component 914 and the second fixing component 924. The cable 932 may be made of a deformable and inelastic material, e.g., a metal, an alloy. The first guiding rail 916 may be fixed-connected to the first straight section 936 of the tube 931, and the second guiding rail 926 may be fixed-connected to the second straight section 938 of the tube 931. In some embodiments, the first guiding rail 916 and/or the second guiding rail 926 may be omitted. Alternatively, the first guiding rail 916 and/or the second guiding rail 926 may be integrated with the first straight section 936 and/or the second straight section 938.

In some embodiments, a user may pull the first fixing component 914 and/or the second fixing component 924 to move the X-ray detector 912 and the weight. For example, the user may pull the first fixing component 914, moving the X-ray detector 912 in the forward direction of X-axis. The cable 932 may pull the weight 922 in a backward direction of X-axis. As another example, the user may pull the second fixing component 924, and move the weight 922 in the forward direction of X-axis. The cable 932 may pull the X-ray detector 912 in the backward direction of X-axis. In some embodiments a computing device (e.g., the processing device 140, the terminal 130) may generate a desired SID based on certain preset rules or regulations and the information of the object. The computing device may also determine a current position of the X-ray detector 912 and a target position of the X-ray detector 912 based on the desired SID. The computing device may also determine the movement of the X-ray detector 912 to the target position to meet the desired SID. The computing device may then generate and send instructions of rotation time and/or rotation speed based on the movement of the X-ray detector 912 to the first weight balancing mechanism 900 to move the X-ray detector 912 to the target position so that the desired SID may be satisfied.

Figure 10:
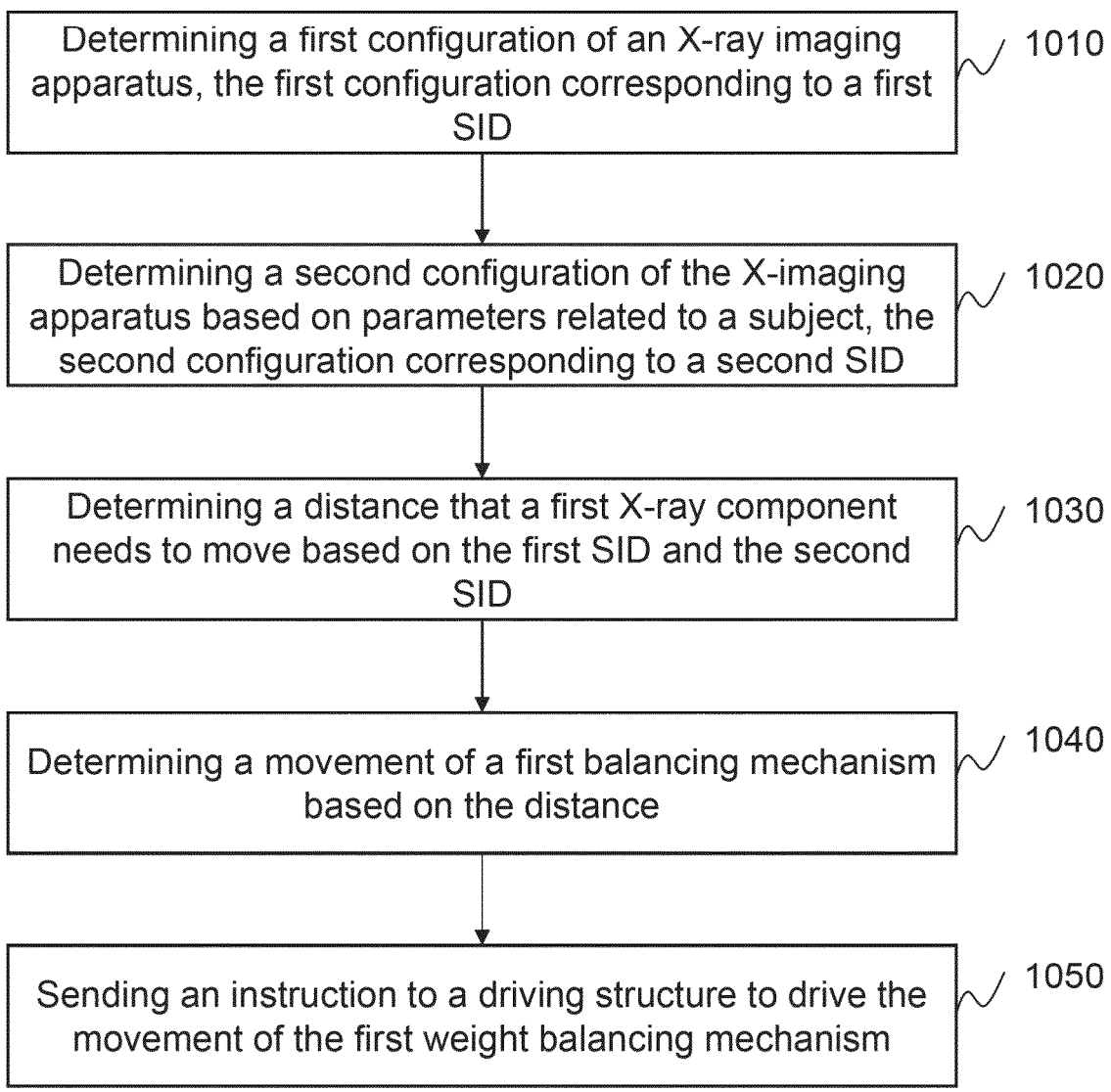
FIG. 10 is a flowchart illustrating an exemplary process for driving a first weight balancing mechanism according to some embodiments of the present disclosure.

FIG. 10 is a flowchart illustrating an exemplary process for driving a first weight balancing mechanism according to some embodiments of the present disclosure. The process 1000 may be implemented in the X-ray imaging system 100 illustrated in FIG. 1. For example, at least some steps of the process 1000 may be stored in the storage device 150 in the form of instructions (e.g., an application), and invoked and/or executed by the processing device 140. The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1010, the processing device 140 may determine a first configuration of an X-ray imaging apparatus (e.g., the X-ray imaging apparatus 110). The first configuration of an X-ray image apparatus may be an initial configuration of the X-ray imaging apparatus. In some embodiments, the processing device 140 may provide the first configuration of the X-ray image apparatus by sending instructions to an arm, a supporting structure, a vertical component, and/or a base component to move them to their corresponding initial positions. Alternatively or additionally, the first configuration of the X-ray imaging apparatus may be configured by a user.

The X-ray imaging apparatus may include an arm (e.g., the arm 113, the arm 230, the arm 330), a first X-ray component (e.g., the first X-ray component 310), and a second X-ray component (e.g., the second X-ray component 320). The arm may include a first end and a second end. In some embodiments, the first end may include a first weight balancing mechanism (e.g., the first weight balancing mechanism 340, the first weight balancing mechanism 400, the first weight balancing mechanism 700, the first weight balancing mechanism 800, the first weight balancing mechanism 800). The first X-ray component may be at the first end of the arm, and the second X-ray component may be at the second end of the arm. The first X-ray component and the second X-ray component may be opposite to each other. The first X-ray component may include an X-ray tube (e.g., the X-ray tube 111, the X-ray tube 210), and the second X-ray component may include an X-ray detector (e.g., the X-ray detector 112, the X-ray detector 220). Alternatively, the first X-ray component may include an X-ray detector, and the second X-ray component may include an X-ray tube. The X-ray tube may be configured to generate X-rays. The X-ray detector may be configured to receive at least part of the X-rays generated by the X-ray tube. A distance between the X-ray tube and the X-ray detector may be referred to as a SID. The first configuration may correspond to a first SID of the X-ray imaging apparatus 110.

In 1020, the processing device 140 may determine a second configuration of the X-ray imaging apparatus based on parameters related to an object. The second configuration may correspond to a second SID of the X-ray imaging apparatus 110. The parameters related to the object may include specifics of the object (e.g., gender, height, weight), a section of the object to be scanned (e.g., a head, a chest), etc.

Different information may be associated with different SIDs. For example, if a section of the object has a large size and requires a low precision, a high SID may be required; if a section of the object has a small size and requires a high precision, a low SID may be required.

In 1030, the processing device 140 may determine a distance that the first X-ray component needs to move based on the first SID and the second SID. In some embodiments, a second end may include a second weight balancing mechanism similar to the first weight balancing mechanism. The second X-ray component may move relative to the second weight balancing mechanism. In a case that the first X-ray component and the second X-ray component are moving in opposite directions, the distance determined in 1030 may be a sum of the distance that the first X-ray component and the second X-ray component need to move. In some embodiments, the distance may be determined based a difference between the first SID and the second SID.

In 1040, the processing device 140 may determine a movement of the first weight balancing mechanism based on the distance that the first X-ray component needs to move. The first weight balancing mechanism may include a weight (e.g., the weight 344, the weight 422, the weight 722, the weight 822, the weight 922) and a driving structure (e.g., the driving structure 342, the driving structure 430, the driving structure 730, the driving structure 830, the driving structure 930). The movement of the first weight balancing mechanism may include a movement of the weight and a movement (or a rotation, a change in current) of the driving structure. The movement direction of the first X-ray component may be opposite to the movement direction of the weight.

In 1050, the processing device 140 may send an instruction to the driving structure of the first weight balancing mechanism to drive the movement of the first weight balancing mechanism. In some embodiments, for different first weight balancing mechanisms, the instruction may include different information, for example, the number of cycles that a gear needs to rotate (e.g., the first weight balancing mechanism 400), a distance that a rack needs to move (e.g., the first weight balancing mechanism 400), a number of cycles that a lead screw needs to rotate (e.g., the first weight balancing mechanism 700), the current in the connecting wires of an electromagnet (e.g., the first weight balancing mechanism 800), a distance that a wire needs to move (e.g., the first weight balancing mechanism 900), etc. In some embodiments, the driving structure may receive the instruction. In response to the instruction, the driving structure may drive the first X-ray component and the weight to move to target positions. The movement of the weight may be configured to maintain the center of gravity of the first end unchanged that caused by the movement of the X-ray detector.

FIG. 11 is a flowchart illustrating an exemplary process for driving a first weight balancing mechanisms according to some embodiments of the present disclosure. The process 1100 may be implemented in the X-ray imaging system 100 illustrated in FIG. 1. For example, the process 1100 may be stored in the storage device150 in the form of instructions (e.g., an application), and invoked and/or executed by the processing device 140. The operations of the illustrated process presented below are intended to be illustrative. In some embodiments, the process 1100 may be accomplished with one or more additional operations not described, and/or without one or more of the operations discussed. Additionally, the order in which the operations of the process 1100 as illustrated in FIG. 11 and described below is not intended to be limiting. In some embodiments, step 1050 of the process 1000 may be performed according to the process 1100.

In 1110, the processing device 140 may move the first X-ray component by the driving structure in a first direction with respect to the first weight balancing mechanism. In some embodiments, the driving structure may include a gear structure (as shown as 600 in FIG. 6A, and 620 in FIG. 6B), a lead screw structure (as shown as 734 in FIG. 7), a magnetism structure (as shown as 832 in FIG. 8), a tensile structure (as shown as 932 in FIG. 9), etc. In response to an instruction, the driving structure may drive the first X-ray component to move in a first direction (e.g., the X-direction). The first direction may be a direction of toward or away a second end of the arm. The driving structure may drive the first X-ray component to move to a specific position to meet the second SID of the X-ray imaging apparatus.

In 1120, the processing device 140 may move the weight of the first weight balancing mechanism by the driving structure in a second direction opposite to the first direction. In some embodiments, the weight of the first X-ray component may be the same as or different from the weight of the weight. The driving structure may move the weight such that the center of gravity of the first end unchanged.

It should be noted that the above description of the process 1100 is provided for the purposes of illustration, and is not intended to limit the scope of the present disclosure. For persons having ordinary skills in the art, multiple variations and modifications may be made under the teachings of the present disclosure. However, those variations and modifications do not depart from the scope of the present disclosure. In some embodiments, steps 1110 and 1120 may be performed simultaneously. For example, the processing device 140 may drive the driving structure, driving the first X-ray component and the weight to move simultaneously. In some embodiments, step 1110 may be performed after step 1120. For example, a user may manually control the weight to move, and the driving structure may drive the first X-ray component to move to meet a specific SID. Alternatively, the user may manually control the first X-ray component to move to meet a specific SID, and the driving structure may drive the weight to move in an opposite direction to compensate the change of the center of gravity of the first end.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially," For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
a processing device, configured to:
determine a first configuration of an X-ray imaging apparatus, the first configuration corresponding to a first Source Image Distance (SID), wherein the X-ray imaging apparatus includes:

an arm including a first end and a second end, the first end including a first weight balancing mechanism, the first weight balancing mechanism including a driving structure and a weight;

a first X-ray component arranged at the first end of the arm, wherein the first X-ray component includes an X-ray tube configured to generate X-rays; and a second X-ray component arranged at the second end of the arm, the first X-ray component and the second X-ray component being opposite to each other;

determine a second configuration of the X-ray imaging apparatus based on parameters related to a subject, the second configuration corresponding to a second SID;

determine a distance that the first X-ray component needs to move based on the first SID and the second SID;

determine a movement of the first weight balancing mechanism based on the distance that the first X-ray component needs to move; and transmit an instruction to the driving structure to drive the movement of the first weight balancing mechanism, wherein the driving structure includes a lead screw, and the instruction is associated with a number of rotations of the lead screw.

2. The system of claim 1, wherein the instruction includes:
a first instruction of moving the first X-ray component on the first end by the driving structure in a first direction with respect to the first weight balancing mechanism; and
a second instruction of moving the weight by the driving structure in a second direction opposite to the first direction.

3. The system of claim 1, wherein the driving structure further includes a gear, and the instruction is further associated with a number of rotations of the gear.

4. The system of claim 1, wherein the driving structure further includes a rack, and the instruction is further associated with a distance of movement of the rack.

5. The system of claim 1, wherein the driving structure further includes an electromagnet, and the instruction is further associated with a change of current in connecting wires of the electromagnet.

6. The system of claim 1, wherein the driving structure further includes a cable, and the instruction is further associated with a distance of movement of the cable.

7. The system of claim 1, wherein the first weight balancing mechanism is configured to maintain a center of gravity of the first end unchanged when the X-ray imaging apparatus changes from the first configuration to the second configuration.

8. The system of claim 1, wherein the second end includes a second weight balancing mechanism, and the processing device is further configured to:
determine a distance that the second X-ray component needs to move based on the first SID and the second SID; and
determine a movement of the second weight balancing mechanism based on the distance that the second X-ray component needs to move.

9. The system of claim 1, wherein the second X-ray component includes an X-ray detector configured to receive at least part of the X-rays generated by the first X-ray component.

10. A method implemented on a computing device having at least one processor and at least one storage device, the method comprising:
determining a first configuration of an X-ray imaging apparatus, the first configuration corresponding to a first Source Image Distance (SID), wherein the X-ray imaging apparatus includes:
an arm including a first end and a second end, the first end including a first weight balancing mechanism, the first weight balancing mechanism including a driving structure and a weight;
a first X-ray component arranged at the first end of the arm, wherein the first X-ray component includes an X-ray tube configured to generate X-rays; and
a second X-ray component arranged at the second end of the arm, the first X-ray component and the second X-ray component being opposite to each other;
determining a second configuration of the X-ray imaging apparatus based on parameters related to a subject, the second configuration corresponding to a second SID;
determining a distance that the first X-ray component needs to move based on the first SID and the second SID;
determining a movement of the first weight balancing mechanism based on the distance that the first X-ray component needs to move; and
transmitting an instruction to the driving structure to drive the movement of the first weight balancing mechanism, wherein the driving structure includes a lead screw, and the instruction is associated with a number of rotations of the lead screw.

11. The method of claim 10, wherein the instruction includes:
a first instruction of moving the first X-ray component on the first end by the driving structure in a first direction with respect to the first weight balancing mechanism; and
a second instruction of moving the weight by the driving structure in a second direction opposite to the first direction.

12. The method of claim 10, wherein the driving structure further includes a gear, and the instruction is further associated with a number of rotations of the gear.

13. The method of claim 10, wherein the driving structure further includes a rack, and the instruction is further associated with a distance of movement of the rack.

14. The method of claim 10, wherein the driving structure further includes an electromagnet, and the instruction is further associated with a change of current in connecting wires of the electromagnet.

15. The method of claim 10, wherein the driving structure further includes a cable, and the instruction is further associated with a distance of movement of the cable.

16. The method of claim 10, wherein the first weight balancing mechanism is configured to maintain a center of gravity of the first end unchanged when the X-ray imaging apparatus changes from the first configuration to the second configuration.

17. The method of claim 10, wherein the second end includes a second weight balancing mechanism, and the method further comprises:
determining a distance that the X-ray component needs to move based on the first SID and the second SID; and
determining a movement of the second weight balancing mechanism based on the distance that the second X-ray component needs to move.

18. A non-transitory computer readable medium comprising executable instructions that, wherein when executed by at least one processor, the executable instructions cause the at least one processor to effectuate a method comprising:
- determining a first configuration of an X-ray imaging apparatus, the first configuration corresponding to a first Source Image Distance (SID), wherein the X-ray imaging apparatus includes:
  - an arm including a first end and a second end, the first end including a first weight balancing mechanism, the first weight balancing mechanism including a driving structure and a weight;
  - a first X-ray component arranged at the first end of the arm, wherein the first X-ray component includes an X-ray tube configured to generate X-rays; and
  - a second X-ray component arranged at the second end of the arm, the first X-ray component and the second X-ray component being opposite to each other;
- determining a second configuration of the X-ray imaging apparatus based on parameters related to a subject, the second configuration corresponding to a second SID;
- determining a distance that the first X-ray component needs to move based on the first SID and the second SID;
- determining a movement of the first weight balancing mechanism based on the distance that the first X-ray component needs to move; and
- transmitting an instruction to the driving structure to drive the movement of the first weight balancing mechanism, wherein the driving structure includes a lead screw, and the instruction is associated with a number of rotations of the lead screw.

* * * * *